United States Patent [19]

Shimano et al.

[11] 4,264,721
[45] Apr. 28, 1981

[54] COLOR PHOTOGRAPHIC MATERIALS

[75] Inventors: Shinji Shimano, Odawara; Tsuneo Wada, Sagamihara; Katsuo Mogaki, Isehara; Shinichi Nakamura, Odawara; Kouji Tokitou, Hachioji, all of Japan

[73] Assignee: Konishiroku Photo Industry Co., Ltd., Odawara, Japan

[21] Appl. No.: 89,252

[22] Filed: Oct. 29, 1979

[30] Foreign Application Priority Data

Oct. 30, 1978 [JP] Japan ................. 53-133954

[51] Int. Cl.$^3$ .............................................. G03C 1/40
[52] U.S. Cl. ...................................... 430/551; 430/351; 430/557; 430/558; 430/611; 430/614; 430/963
[58] Field of Search ............... 430/551, 372, 557, 558, 430/611, 614, 963, 351

[56] References Cited

U.S. PATENT DOCUMENTS

| 3,645,738 | 2/1972 | Willems et al. ................. 430/963 |
| 3,718,468 | 2/1973 | Berthold et al. ................ 430/963 |
| 3,901,709 | 8/1975 | Ebato et al. .................... 430/614 |
| 4,021,248 | 5/1977 | Shiba et al. .................... 430/611 |

Primary Examiner—J. Travis Brown
Attorney, Agent, or Firm—Haseltine and Lake

[57] ABSTRACT

A color photographic material comprising, on a support, a silver halide emulsion layer which contains a 2-equivalent α-acylacetamide yellow coupler carrying a nitrogen-containing heterocyclic coupling off group, joined to a nitrogen atom, as being releasable upon the reaction with an oxidation product of a color developing agent and a compound of the following formula (I) or its tautomer:

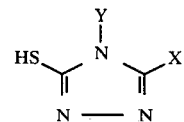

wherein X and Y are as herein defined, is described.

3 Claims, No Drawings

COLOR PHOTOGRAPHIC MATERIALS

This invention relates to color photographic photosensitive materials suitable for high temperature and high speed treatments and more particularly, to silver halide-based color photographic photosensitive materials which are able to yield a yellow dye image of low fog density even by high temperature development of above 30° C. and which are improved in fastness or sharpness of images.

In recent years, there has been a strong demand of color photographic material which are developable expeditiously within a short time, say, within 6 minutes and especially within 3 minutes.

In the rapid processing for photographic photosensitive materials for which many effects have been made, fogging takes place frequently and even extremely especially when the rapid treatment is conducted at high temperatures above 30° C. In order to suppress the occurrence of fogging, various attempts have been made including, for example, a use of so-called DIR compounds which are able to release a fogging inhibitor by reaction with oxidation products of color developing agent, a use of phenol derivatives and particularly hydroquinone derivatives, and a use of mercapto compounds such as 2-mercapto-benzimidazole, 3-mercapto-4-phenyl-1,2,4-triazole, 1-phenyl-5-mercaptotetrazole and the like. However, those compounds have a disadvantage that they tend to lower the sensitivity of photographic materials or deteriorate their tone wedge, or to gradually lower the sensitivity with a lapse of time.

In order to overcome the disadvantages, there has been made another attempt, such as in Japanese Laid-open Publication No. 51-27935, to use a specific type of coupler in combination with mercapto compounds having a water-soluble group such as, for example, —SO₃H, —COOH, —OH or the like. By this, the above-described disadvantage is overcome to an extent, however, such attempt not only is not sufficient, but also produces a new defect. That is, in the above-described attempt, the photographic photosensitive material is incorporated with mercapto compounds having a water-soluble group and when such photographic photosensitive material is processed, the mercapto compound is entrained into a developer though very small in amount. If a great deal of the materials are processed, the compound is accumulated in the developer, resulting in a disadvantage that the developing velocity becomes slower or in the case of multi-layered color photographic photosensitive materials, the color balance is lost. This becomes pronounced especially when a developer which has been recovered and regenerated is used. That is, when the photographic photosensitive materials which comprise mercapto compounds having water-soluble groups as aforesaid are processed, the mercapto compound which has been migrated in a small amount into the developer is not removed in a process where the developer is repeatedly recovered and regenerated and its amount is gradually increased and accumulated, thus presenting a serious problem.

A first object of the invention is to provide a silver halide color photographic material which is suppressed in occurrence of fogging where processed by high temperature development and particularly at temperatures above 30° C.

A second object of the invention is to provide a silver halide color photographic material which suffers no fogging even when subjected to high temperature developing treatments and in which it is reduced to a degree as small as possible to allow compounds, which are accumulated in a developer and produce harmful actions, to be dissolved out from the photographic material, i.e. it can realize stable treatments when used for repeated treatments.

A third object of the invention is to provide a silver halide color photographic material which shows a suppressed degree of fogging and an improved storing stability.

We have found that the above objects can be achieved by a color photographic material which comprises, on a support, a photosensitive silver halide emulsion layer which contains a combination of at least one 2-equivalent α-acylacetoamide yellow coupler having a group, joined to a nitrogen atom, which is able to be released by reaction with an oxidation product of an aromatic primary amine color developing agent and at least one compound represented by the following general formula (I) or its tautomer.

General formula (I)

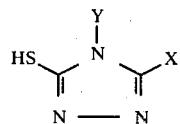

In the general formula (I), X represents an —NHCOR₁ radical or an —NHSO₂R₂ wherein R₁ and R₂ independently represent (1) an alkyl group (e.g. those having preferably 1–12 carbon atoms such as a methyl group, an ethyl group, a propyl group, an octyl group and the like) which is unsubstituted or substituted with a halogen atom (e.g. a fluorine atom, a chlorine atom or the like), an alkoxy group (e.g. a methoxy group, an ethoxy group, an octyloxy group, a decyloxy group or the like), an aryloxy group (e.g. a phenoxy group, a naphthoxy group or the like), an alkylthio group (e.g. a methylthio group, an ethylthio group, an octylthio group or the like), an aryl group (e.g. a phenyl group, a naphtyl group or the like), an arylthio group (e.g. a phenylthio group, a naphthylthio group or the like), or a cyano group, or (2) an aryl group (e.g. a phenyl group, a naphthyl group or the like), a cycloalkyl group (e.g. a cyclohexyl group or the like), an aralkyl group (e.g. a benzyl group, a phenethyl group or the like), or an alkenyl group (e.g. an allyl group or the like), each of which is unsubstituted or substituted with a halogen atom, (a fluorine atom, a chlorine atom or the like), an alkoxy group (e.g. a methoxy group, an ethoxy group, an octyloxy group, a decyloxy group or the like), an aryloxy group (e.g. a phenoxy group, a naphthoxy group or the like), an alkylthio group (e.g. a methylthio group, an ethylthio group, an octylthio group or the like), a cyano group, an alkyl group (e.g. a methyl group, an ethyl group, a propyl group, an octyl group or the like) or a halogen atom-substituted alkyl group, and Y represents (1) a hydrogen atom, (2) an alkyl group (having preferably 1–8 carbon atoms such as, for example, a methyl group, an ethyl group, a propyl group, an octyl group or the like) which is unsubstituted or substituted with a halogen atom (e.g. a fluorine atom, a chlorine atom or the like), an alkoxy group (e.g. a methoxy group, an ethoxy group, an octyloxy group, a decyloxy group or the like), an aryloxy group (e.g. a phenoxy group, a naphthoxy group or the like), an alkylthio group (e.g. a methylthio group, an ethylthio group, an octylthio group or the like), an arylthio group (e.g. phenylthio group, naphthylthio group or the like) or a cyano group, (3) an aryl group (e.g. a phenyl group, a naphthyl group or the like), a cycloalkyl group (e.g. a cyclohexyl group or the like), an alkenyl group (e.g. an allyl group or the like), or an aralkyl group (e.g. a benzyl group, a phenethyl group or the like), each of which is unsubstituted or substituted with a halogen atom (e.g. a fluorine atom, a chlorine atom or the like), an alkoxy group (e.g. a methoxy group, an ethoxy group, an octyloxy group, a decyloxy group or the like), an aryloxy group (e.g. a phenoxy group, a naphthoxy group or the like), an alkylthio group (e.g. a methylthio group, an ethylthio group, an octylthio group or the like), an arylthio group (e.g. a phenylthio group, a naphthylthio group or the like), a cyano group, an alkyl group (e.g. a methyl group, an ethyl group, a propyl group, an octyl group or the like), or a halogen-substituted alkyl group, or (4) a —COR$_3$ group or an —SO$_2$R$_4$ group, in which R$_3$ and R$_4$ independently represent (1) an alkyl group (e.g. a methyl group, an ethyl group, a propyl group, an octyl group or the like) which is unsubstituted or substituted with a halogen atom (e.g. a fluorine atom, a chlorine atom or the like), an alkoxy group (e.g. a methoxy group, an ethoxy group, an octyloxy group, a decyloxy group or the like), an aryloxy group (e.g. a phenoxy group, a naphthoxy group or the like), an alkylthio group (e.g. a methylthio group, an ethylthio group, an octylthio group or the like), an arylthio group (e.g. phenylthio group, naphthylthio group or the like) or a cyano group, or (2) an aryl group (e.g. a phenyl group, a naphthyl group or the like), an alkenyl group (e.g. an allyl group or the like), an aralkyl group (e.g. a benzyl group, a phenethyl group or the like), or a cycloalkyl group (e.g. a cyclohexyl group or the like), each of which is unsubstituted or substituted with a halogen atom (e.g. a fluorine atom, a chlorine atom, or the like), an alkoxy group (e.g. a methoxy group, an ethoxy group, an octyloxy group, a decyloxy group or the like), an aryloxy group (e.g. a phenoxy group, a naphthoxy group or the like), an alkylthio group (e.g. a methylthio group, an ethylthio group, an octylthio group or the like), an arylthio group (e.g. a phenylthio group, a naphthylthio group or the like), a cyano group, an alkyl group (e.g. a methyl group, an ethyl group, a propyl group, an octyl group or the like), or a halogen-substituted alkyl group.

3-Mercapto-1,2,4-triazole represented by the general formula (I) tautomerically behaves as follows:

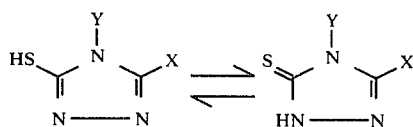

Preferable 2-equivalent α-acylacetoamide yellow couplers useful in the present invention are those expressed by the general formula (II).

General formula (II)

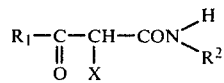

In the general formula (II), R$_1$ is a linear or cyclic alkyl group carrying at its end a tertiary carbon atom directly connecting to the carbonyl group (e.g. a tert-butyl group, a tert-amyl group, an 1,1-dimethylhexyl group, an 1,1-dimethyldecyl group, an 1,1-dimethyltetradecyl group, an 1,1-dimethylhexadecyl group, an 1-bicyclo(3,2,1) octyl group, a 5-norbornene-2-yl group, a 5-pinanyl group, an 1-p-menthene-8-yl group, a bicyclo(3,2,1) oct-5-yl group or the like, or an aryl group (e.g. a phenyl group, a naphthyl group or the like), R$_2$ is an aryl group (e.g. a phenyl group, a naphthyl group or the like) or a heterocyclic group (e.g. a thienyl group, a benzothienyl group, a furyl group, a pyranyl group, a pyrrolyl group, an imidazolyl group, a pyrazolyl group, a pyridyl group, a pyrimidyl group, a pyridazyl group, an indolyl group, an indazolyl group, a quinolyl group, an oxazolyl group, a pyrrolidyl group, a benzoimidazolyl group, a naphthoimidazolyl group, a benzooxazolyl, a naphthooxazolyl group, a thiazolyl group, a benzothiazolyl group, a naphthothiazolyl group, a selenazolyl group, a benzoselenazolyl group or the like), and X is

in which A$_1$ is a group of non-metallic atoms required to form a 4- to 6-membered, netrogen-containing heterocyclic ring, which may further contain a nitrogen, oxygen or sulfur atom as a hetero atom, and which ring may have a substituent.

The above-indicated R$_1$ is preferably a linear or cyclic alkyl group containing 4–18 carbon atoms or a substituted or unsubstituted phenyl group and most preferably a linear alkyl group (especially a tertiary alkyl group) containing 4–18 carbon atoms, or a cyclic alkyl group or a phenyl group each containing 6–18 carbon atoms (which may be substituted with an alkyl group or an alkoxy group containing 1–22 carbon atoms, a halogen atom and/or a carbamoyl group). The R$_2$ is preferably a substituted phenyl group and most preferably a phenyl group substituted at the ortho position with a halogen atom, an alkoxy group containing 1–22 carbon atoms or a phenoxy group (which phenyl group may be further substituted). Further, the substituent is preferred to be a halogen atom, an acyl group, a sulfonyl group, an imido group, an alkoxycarbonyl group, a carbamoyl group, an acylamino group, a sulfamoyl group or a sulfonamido group. The X is preferably a substituted or unsubstituted pyrrole group, a group of atoms required to form a five- or six-membered diazole ring or a group of atoms required to form a four- to six-membered imido ring (and these groups may contain, aside from carbon atoms, an oxygen atom, a sulfur atom, a selenium atom, or a nitrogen atom and preferable examples of X include an succinimido ring group, a maloimido ring group, a phthaloimido ring group, a maleimido ring group, a glutarimido ring group, an 1,2,3,6-tetrahydropyridine-2,6-dione-1-yl group, a 3-isothiazolidinone-1,1-dioxide-2-yl group, a 3,5-dioxo-triazolidine-3-yl(urazol) group, a 2,4-dioxooxazolidine-3-yl group, a 3,5-dioxomorpholine-4-yl group, a 2,4-dioxo-thiazolidine-2-yl group, a 2,4-dioxo-imidazolidine-3-yl(hydantoin) group, a 3-oxo-succinimido ring group, a 2,3,5-trioxo-imidazolidine-4-yl(parabanic acid) group, an 1,3-benzoxazine-2,4(3H)-dione-3-yl group, a 2,4-azetidinedione-1-yl group, a 2H-pyridazine-3-one-2-yl group, a 2-pyridone-1-yl group, a 1H-pyrazine-2-one group, a 3H-pyrimidine-4-one-3-yl group, a 2-pyrazoline-5-one- 1-yl group, an 1H-pyrimidine-2-one-1-yl group, a 2-quinolone-1-yl group, an 1,2,4-as-triazine-5(4H)-one-yl group, a Δ¹-1,2,4-triazine-3-one-4-yl group, a Δ⁵-1,2,3-triazine-4-one-3-yl group, a Δ¹-1,2,3-triazoline-4-one-3-yl group, an 1,3,4-oxadiazoline-2-one-3-yl group, 1,3,4-thiaziazoline-2-one-3-yl group, a Δ⁴-1,2,4-triazoline-3-one-2-yl group, a 1,2,3,4-tetrazoline-5-one-1-yl group, a thiazoline-2-one-3-yl group, an isothiazoline-3-one-2-yl group, an oxazoline-2-one-3-yl group, an 1,3,5-s-triazine-2(1H)-one-1-yl group, 5-imidazoline-4-one-3-yl group, an 1,2,4-s-triazine-3(2H)-one-2-yl group, a 4-imidazoline-2-one-1-yl group, a 3-pyrroline-2-one-1-yl group, an isooxazoline-3-one-2-yl group or the like). Preferable examples of the substituent for the X include a halogen atom, a carboxyl group, an amino group, a linear or branched alkyl group containing 1–22 carbon atoms, an aryl group, a heterocyclic group, an alkoxy group, an acylamino group, and a carbamoyl group. These substituents may be further substituted with any groups.

The compounds of the general formula (I) and the yellow couplers of the general formula (II) both useful in the practice of the invention will be particularly mentioned below, to which the present invention is not limited.

Examples of Compound of General Formula (I)

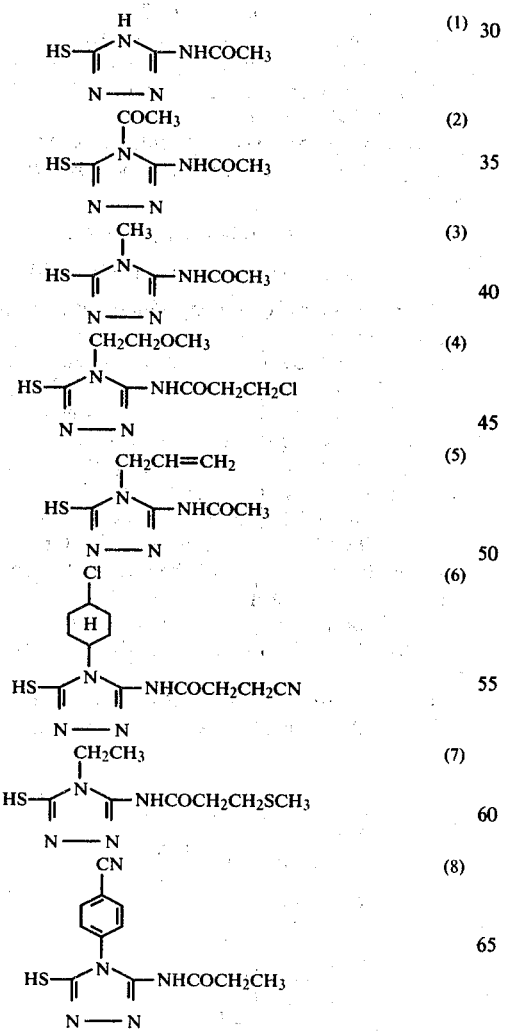

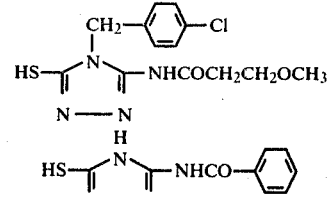

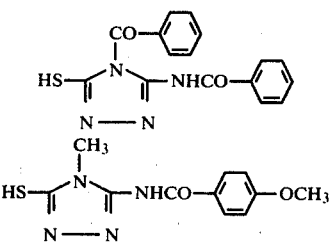

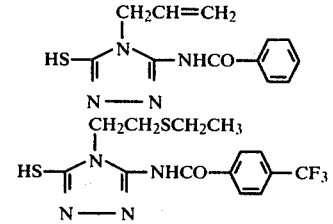

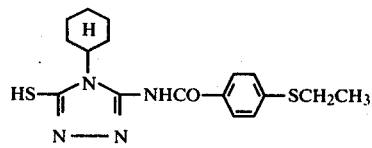

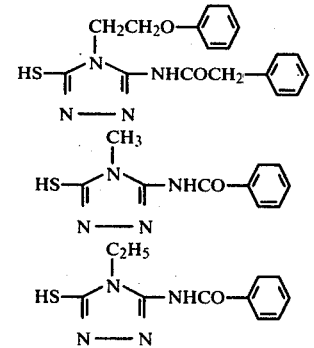

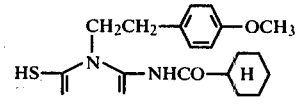

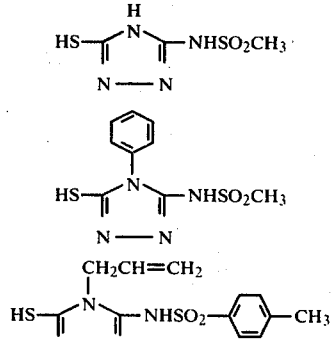

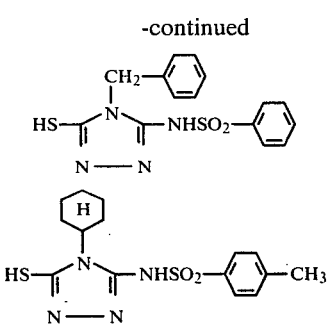

These compounds expressed by the general formula (I) can be prepared according to a known method, in which 3-amino-5-mercapto-1,2,4-triazole which carries hydrogen or is substituted at 4 position is reacted with an acid chloride or sulfonyl chloride in the presence of a suitable hydrochloric acid-removing agent or with an acid anhydride.

The synthetic examples for/some of the above-exemplified compounds will be shown.

Synthetic Example 1

Synthesis of Compound No. (3)

10 g Of 3-amino-4-methyl-5-mercapto-1,2,4-triazole was dispersed in 50 ml of acetic anhydride and 50 ml of acetic acid and refluxed under heating for 6 hours. As the reaction proceeded, the triazole was gradually dissolved. After cooling, the reaction solution was concentrated under reduced pressure to remove acetic acid and the residue was recrystallized from water. Yield: 10 g, Melting Point: 216° C.–218° C.

Elementary Analysis: Calculated C:34.88, H:4.65, N:32.56, S:18.60: Found C:34.91, H:4.60, N:32.60, S:18.65.

Synthetic Example 2

Synthesis of Compound No. (5)

The reaction was conducted similarly to Synthetic Example 1, followed by recrystallizing from water to obtain a reaction product with a melting point of 153°–154° C.

Elementary Analysis: Calculated C:42.42, H:5.05, N:28.28, S:16.16: Found C:42.40, H:5.10, N:28.25, S:16.09.

Synthetic Example 3

Synthesis of Compound Nos. (10) and (11)

10 g Of 3-amino-5-mercapto-1,2,4-triazole was dispersed in 50 ml of chloroform, to which was added 18 ml of triethylamine, followed by cooling the system to below 5° C. To the system was gradually added under agitation 15 ml of benzoyl chloride, followed by agitation for further 4 hours. The reaction mixture was filtered and the solid residue was washed with 100 ml of ethyl alcohol. The resulting colorless crystals were isolated and purified by means of a column chromatography to obtain the compound No. (10) with a melting point of 220° C.–221° C. and the compound No. (11) with a melting point 178° C.–180° C.

Elementary Analysis for Compound No. (10) Calculated C:49:09, H:3.64, N:25.45, S:14.54: Found C:49.10, H:3.58, N:25.41, S:14.50.

Elementary Analysis for Compound No. (11): Calculated C:59.26, H:3.70, N:17.28, S:9.88: Found C:59.30, H:3.58, N:17.25, S:9.80.

Though the structure of the compound No. (11) has been indicated as shown before, it may be considered that the benzoyl group attached to 4 position is located at 1 or 2 position as presumed from tautomers of the starting 3-amino-5-mercapto-1,2,4-triazole. Since the position to which the benzoyl group is attached is not clearly known even when determined by any of existing analyses, the structural formula is expressed as mentioned hereinbefore.

Synthetic Example 4

Synthesis of Compound No. (13)

10 g Of 3-amino-4-allyl-5-mercapto-1,2,4-triazole was dispersed in 50 ml of acetone, to which was added 10 ml of pyridine, followed by gradually dropping 8 ml of benzoyl chloride under agitation at room temperature. After completion of the dropping, the mixture was heated and refluxed for 2 hours. After cooling, the reaction solution was charged into 200 ml of ethyl alcohol and the remaining solids were separated by filtration and recrystallized from a large quantity of ethyl alcohol to obtain 5 g of the intended compound No. (13). Melting Point: 147°–149° C.

Elementary Analysis: Calculated C:55.38, H:4.61, N:21.54, S:12.30: Found C:55.40, H:4.50, N:21.50, S.12.35.

Synthetic Example 5

Synthesis of Compound No. (20)

10 g Of 3-amino-4-phenyl-5-mercapto-1,2,4-triazole was dissolved in 50 ml of dimethylacetamide, to which was further added 15 ml of triethylamine. The mixture was cooled to 5° C., into which was gradually dropped 10 g of methanesulfonyl chloride. After the dropping, the mixture was gradually returned to room temperature, followed by agitation for further 2 hours. The reaction mixture was charged into 500 ml of ethyl alcohol and allowed to stand. The resulting crystals were separated by filtration and recrystallized from dimethylformamide to obtain 3 g of the intended compound No. (19) with a melting point of 153°–154° C.

Elementary Analysis: Calculated C:18.56, H:3.09, N:28.87, S:32.99: Found C:18.50, H:3.00, N:28.59, S:32.58.

Then, examples of the yellow coupler expressed by the general formula (II) will be mentioned.

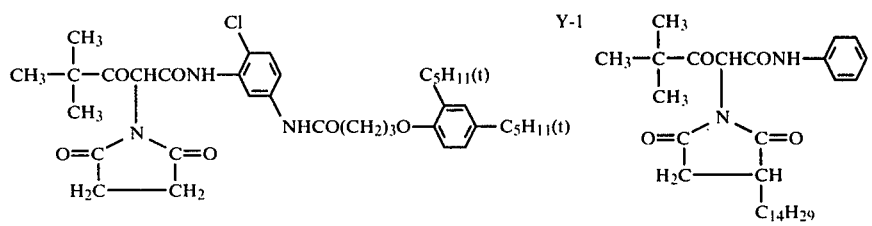

-continued
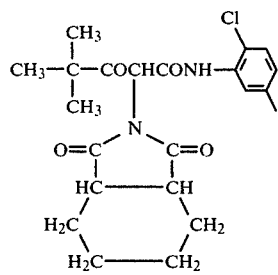 Y-3
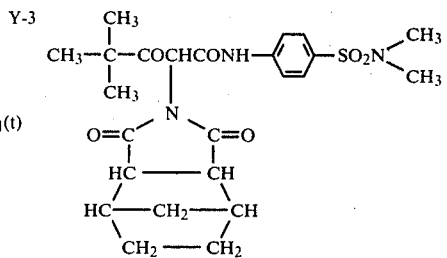 
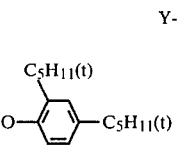 Y-4
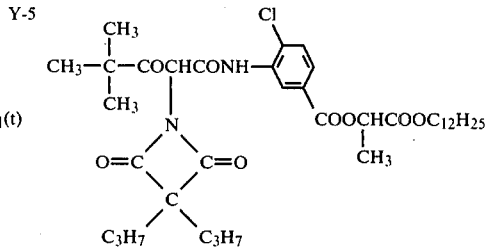
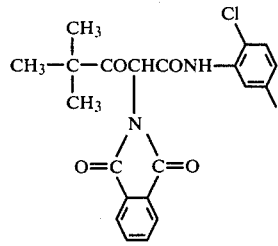 Y-5
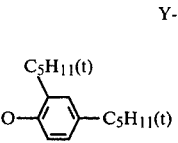 Y-6
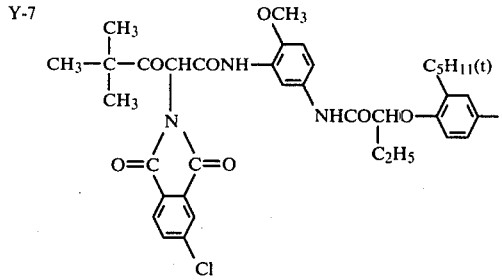
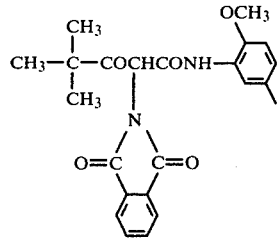 Y-7
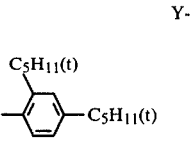 Y-8
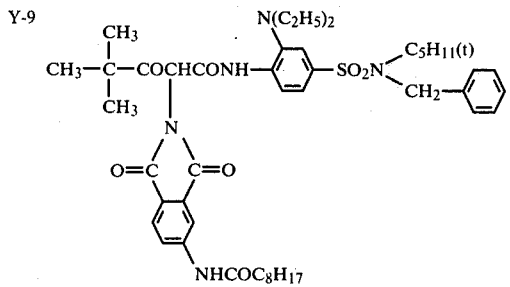
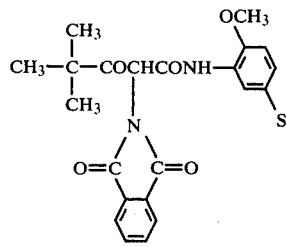 Y-9
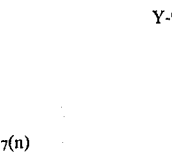 Y-10
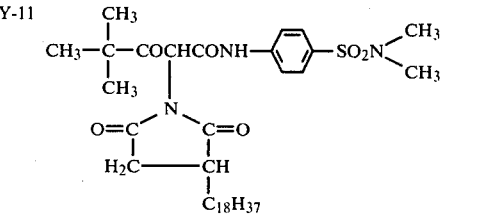
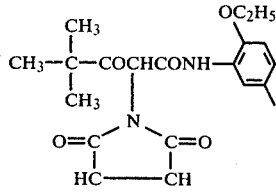 Y-11
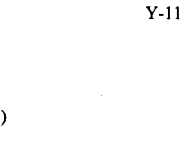 Y-12
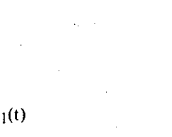
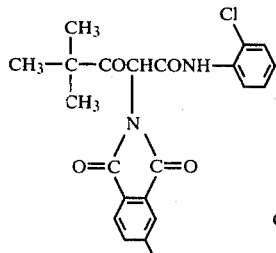 Y-13
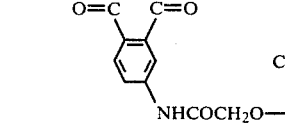

-continued
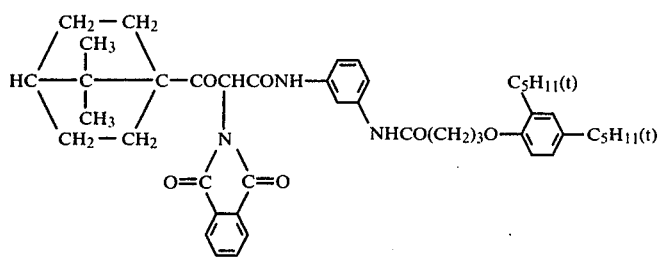
Y-14
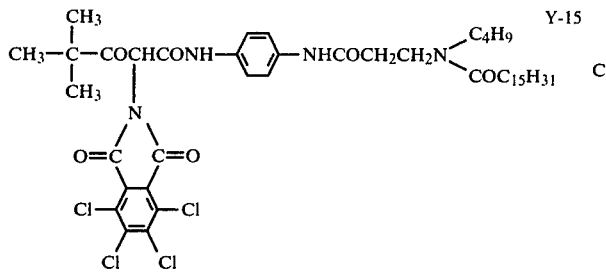
Y-15
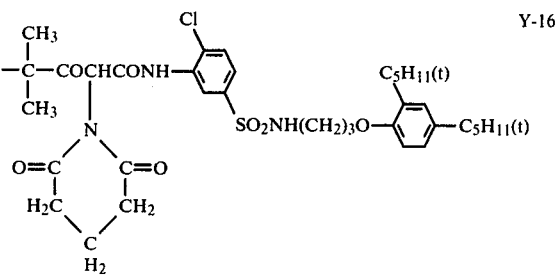
Y-16
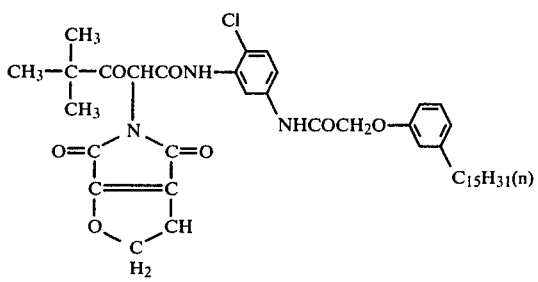
Y-17
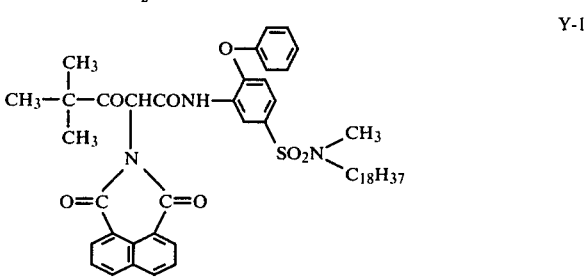
Y-18
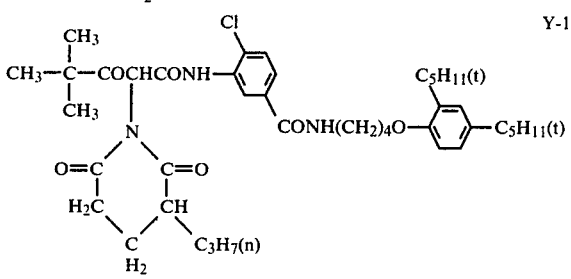
Y-19
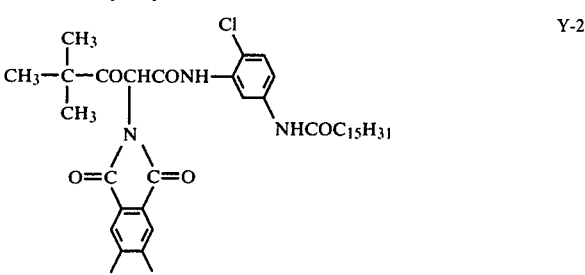
Y-20
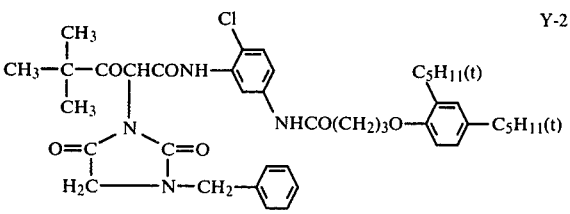
Y-21
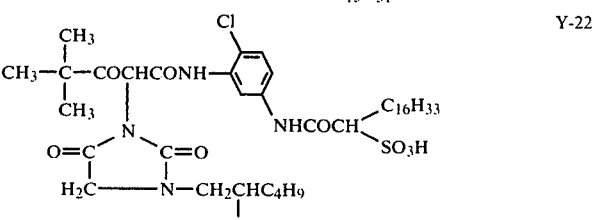
Y-22
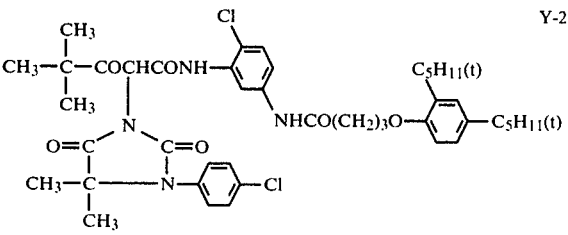
Y-23
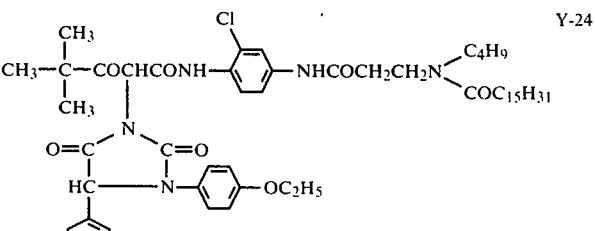
Y-24

-continued
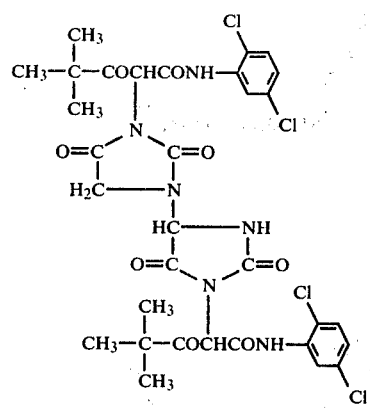 Y-25
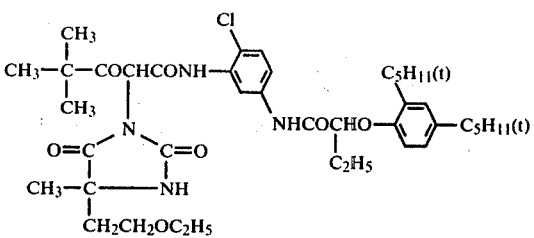 Y-26
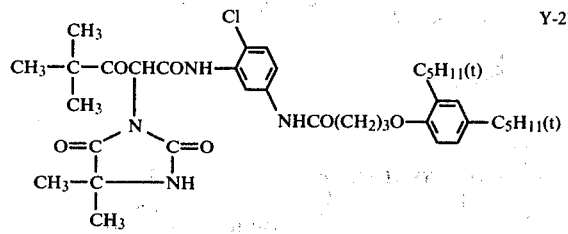 Y-27
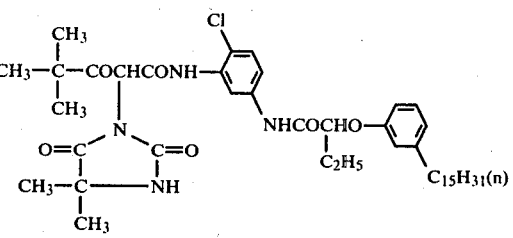 Y-28
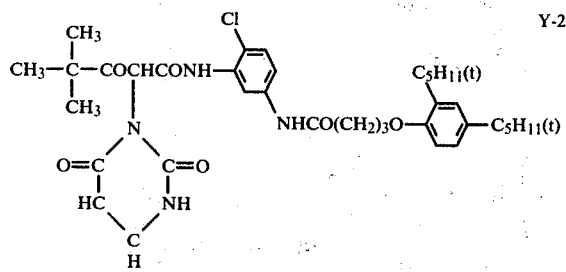 Y-29
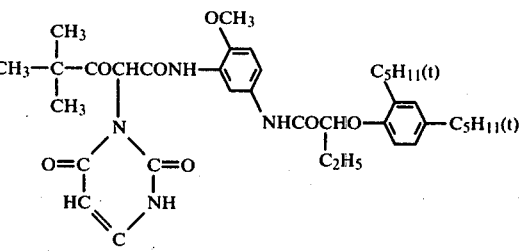 Y-30
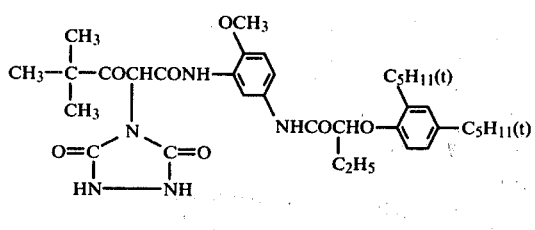 Y-31
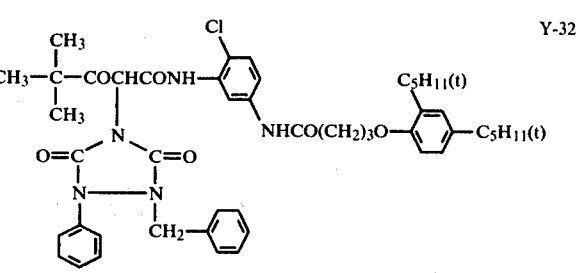 Y-32
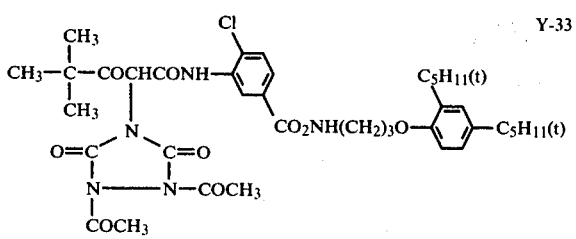 Y-33
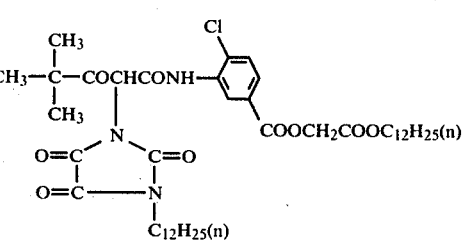 Y-34
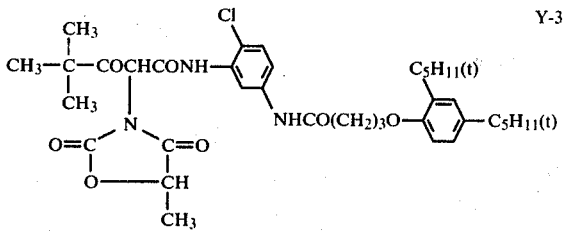 Y-35
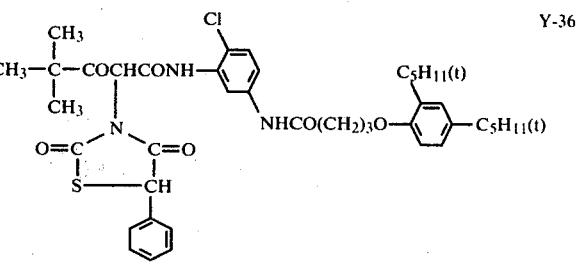 Y-36

-continued
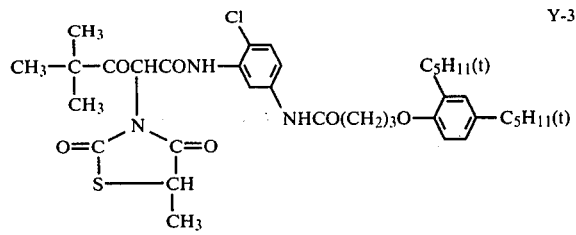
Y-37
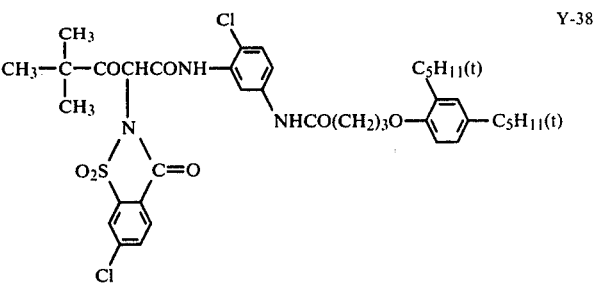
Y-38
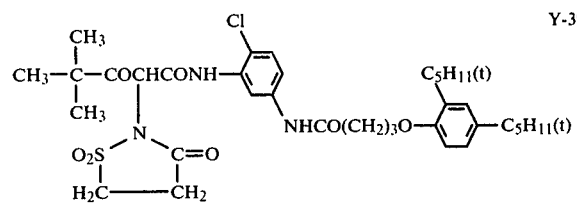
Y-39
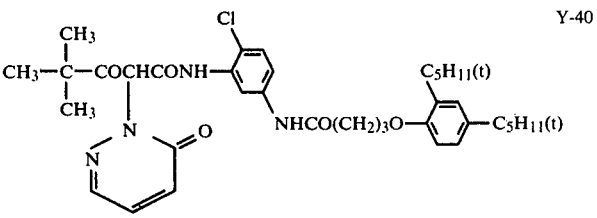
Y-40
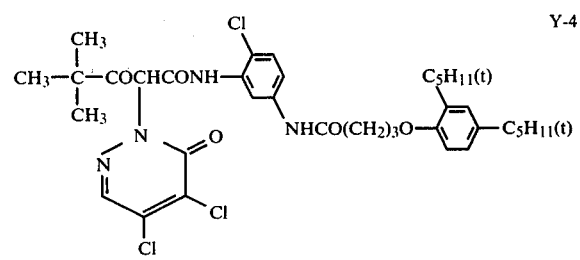
Y-41
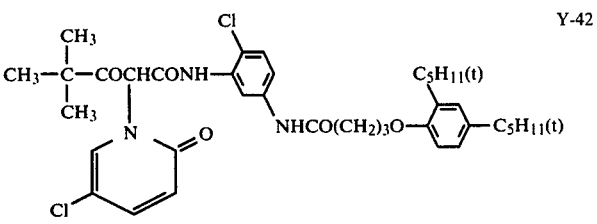
Y-42
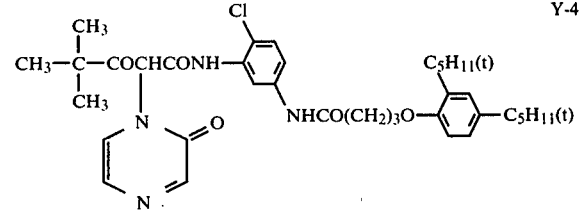
Y-43
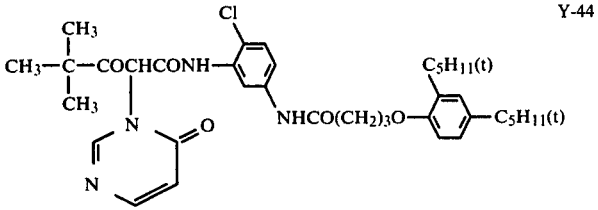
Y-44
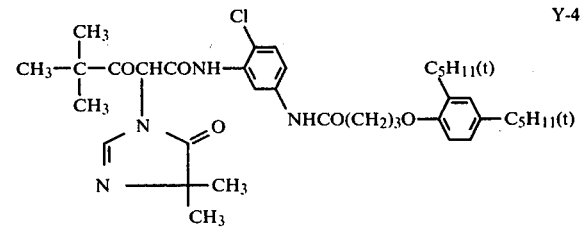
Y-45
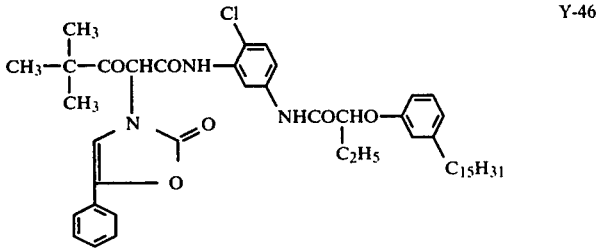
Y-46
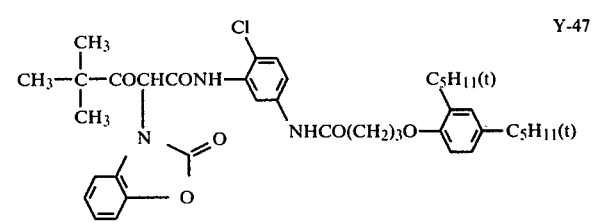
Y-47
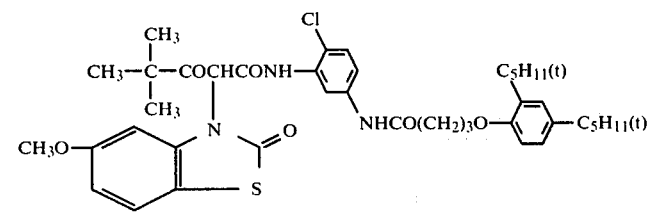
Y-48

-continued
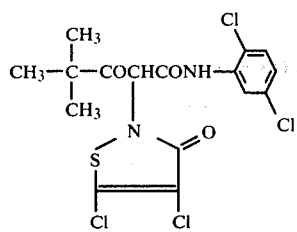 Y-49
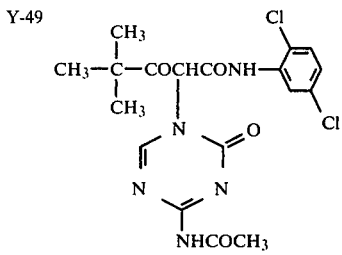 Y-50
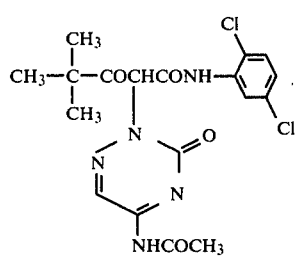 Y-51
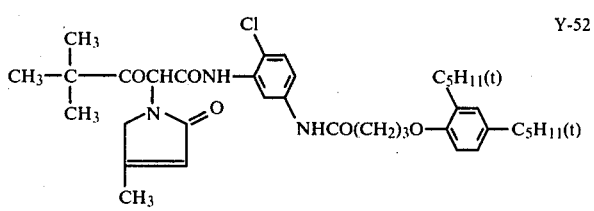 Y-52
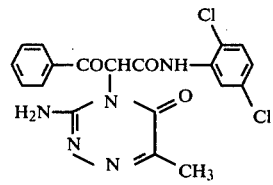 Y-53
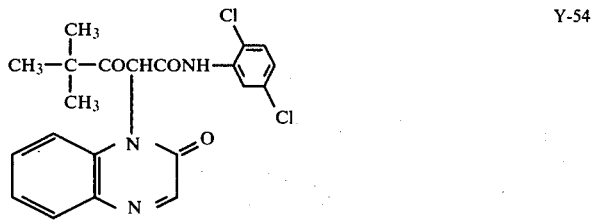 Y-54
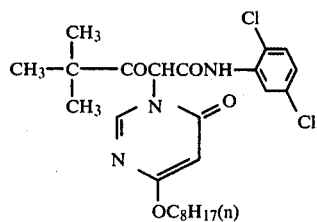 Y-55
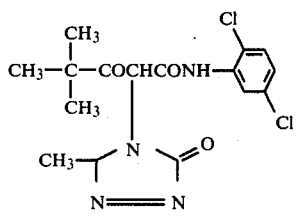 Y-56
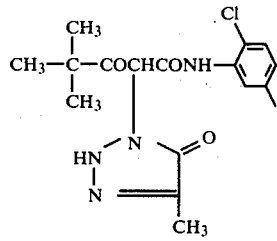 Y-57
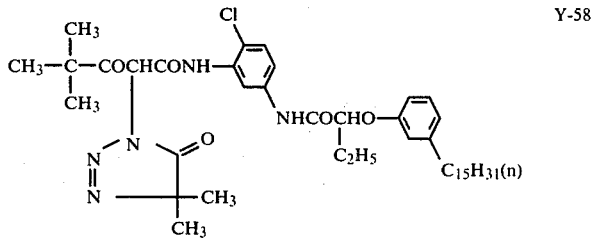 Y-58
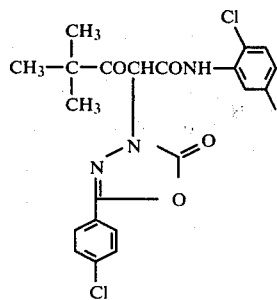 Y-59
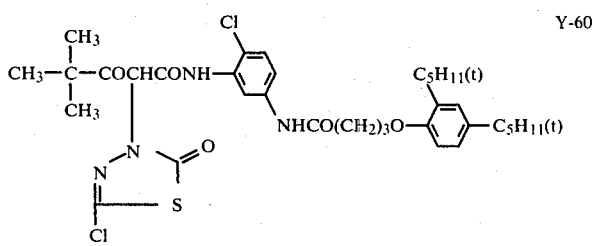 Y-60

-continued
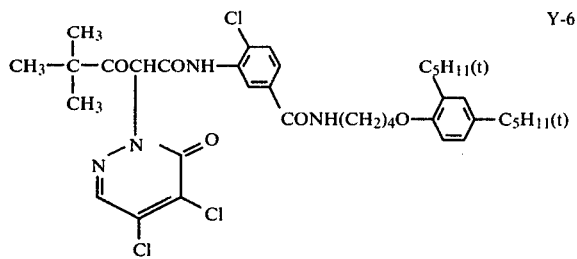 Y-61
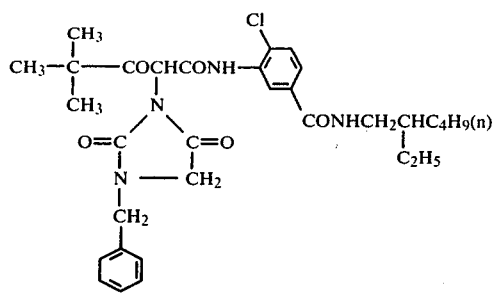 Y-62
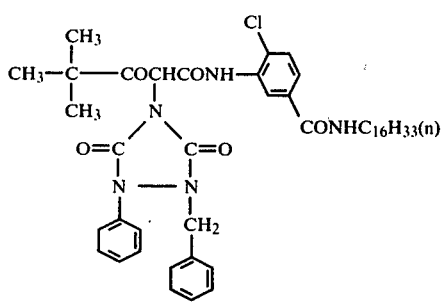 Y-63
Y-64
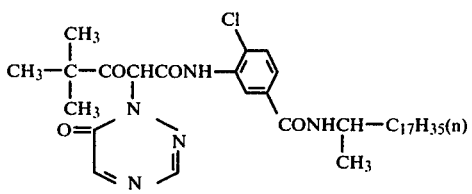 Y-65
Y-66
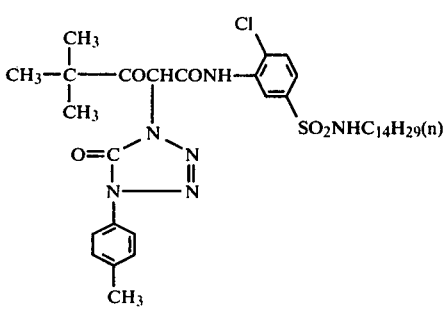 Y-67
Y-68
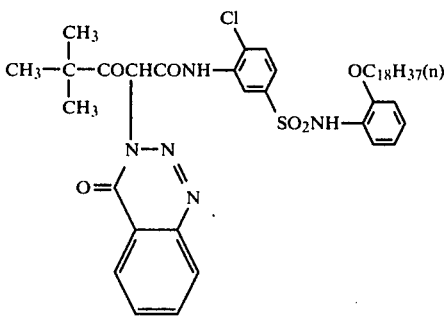 Y-69
Y-70
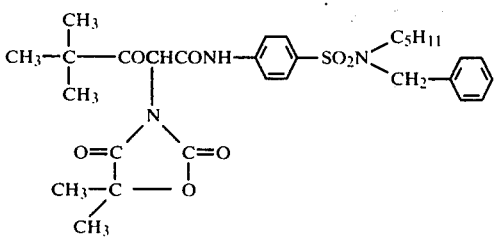 Y-71
Y-72

-continued
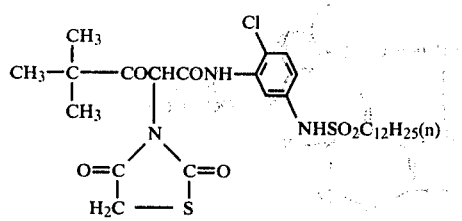 Y-73
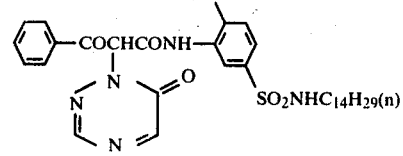 Y-74
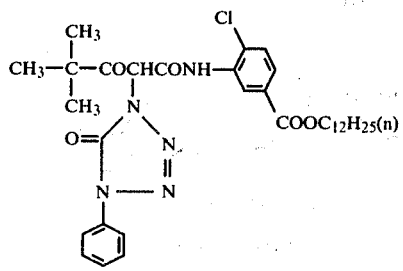 Y-75
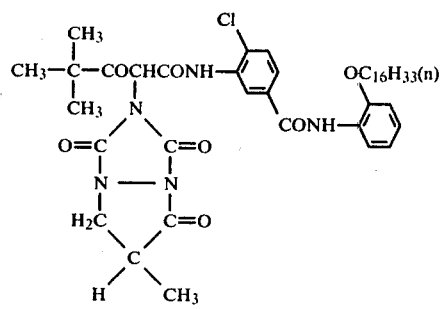 Y-76
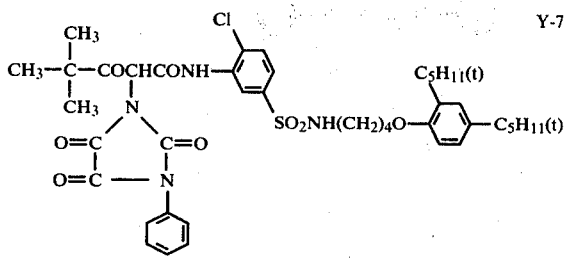 Y-77
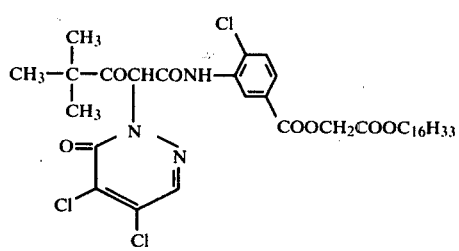 Y-78
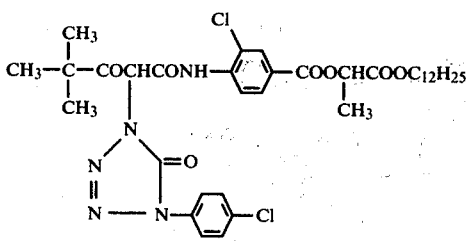 Y-79
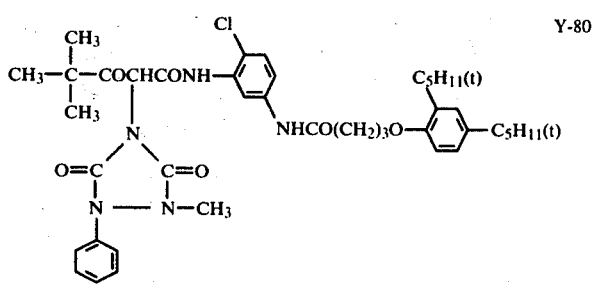 Y-80
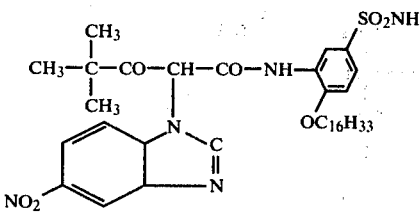 Y-81
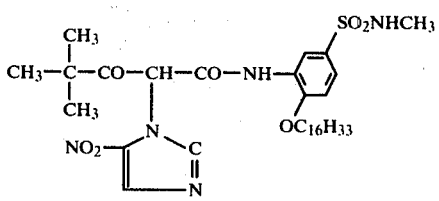 Y-82
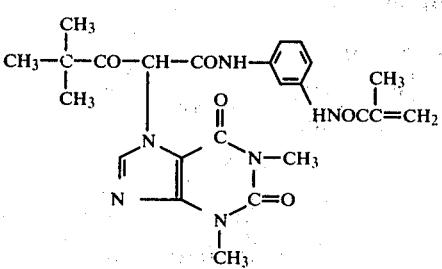 Y-83
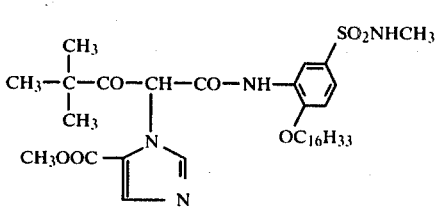 Y-84

-continued
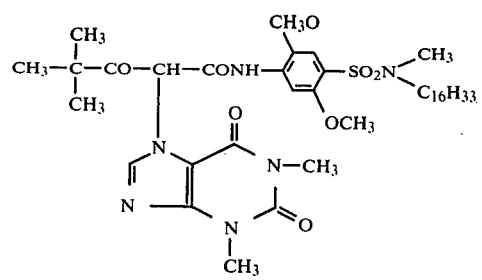 Y-85
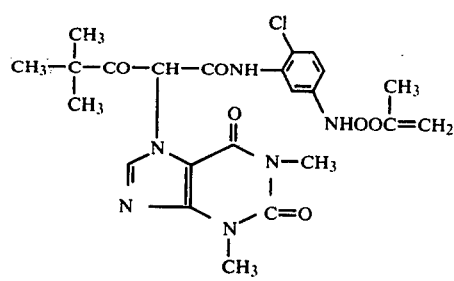 Y-86
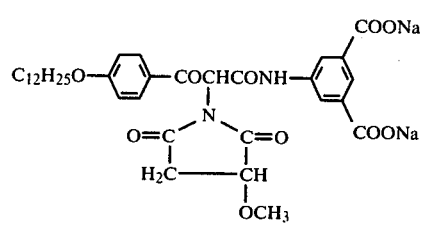 Y-87
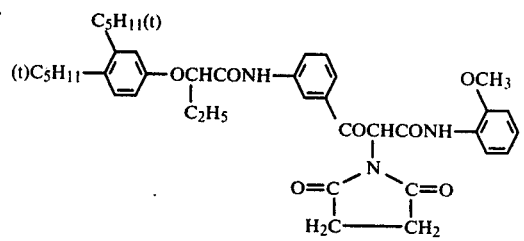 Y-88
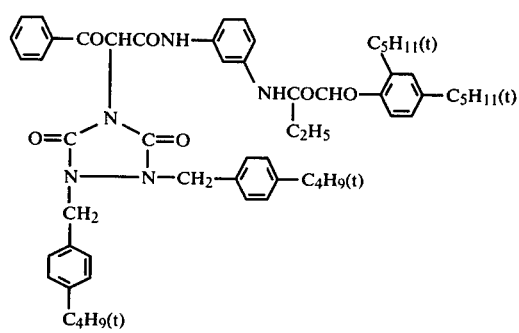 Y-89
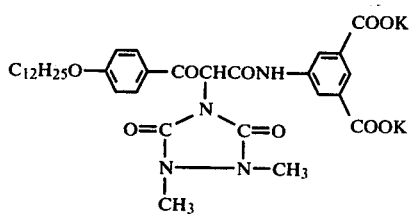 Y-90
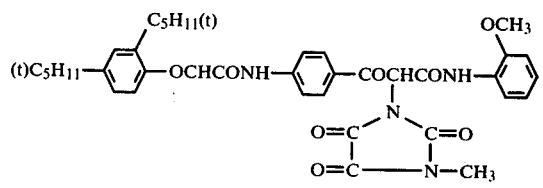 Y-91
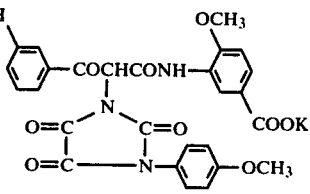 Y-92
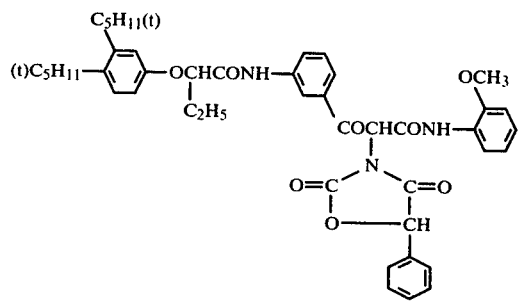 Y-93
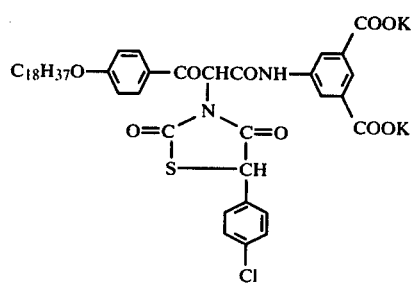 Y-94
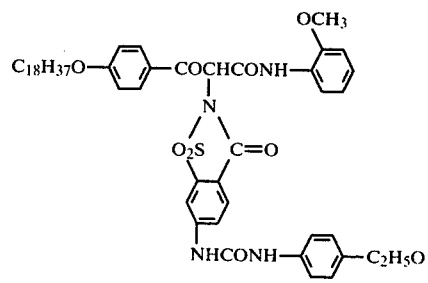 Y-95
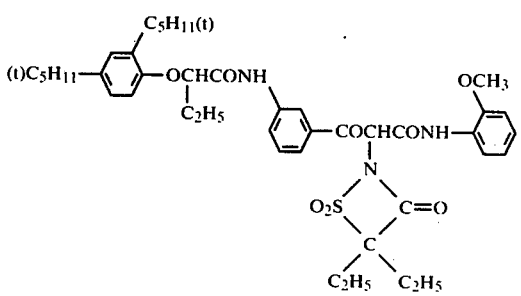 Y-96

-continued
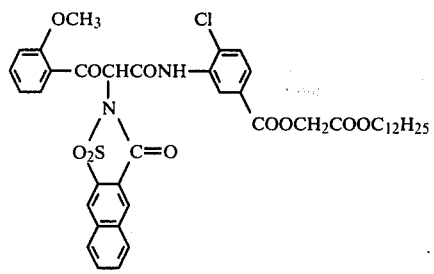 Y-97
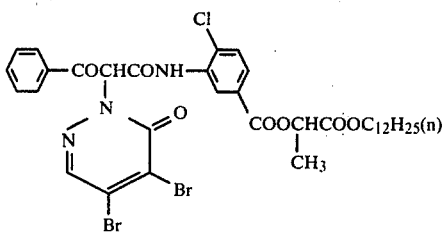 Y-98
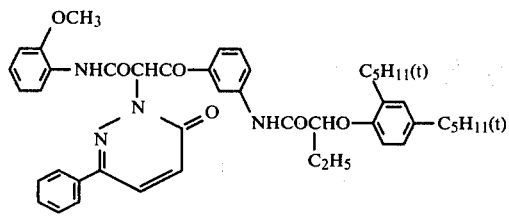 Y-99
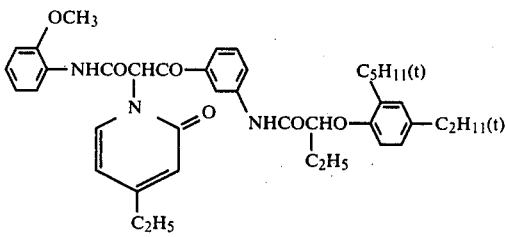 Y-100
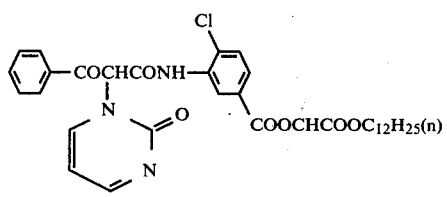 Y-101
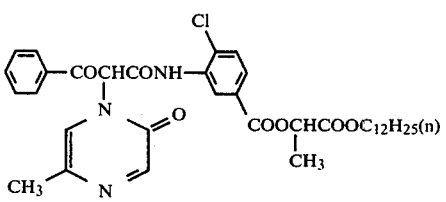 Y-102
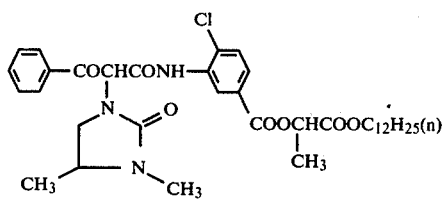 Y-103
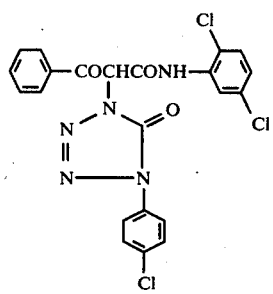 Y-104
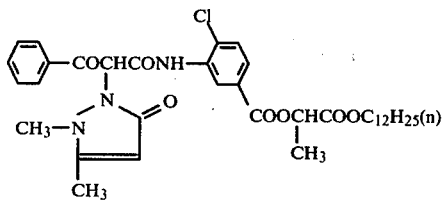 Y-105
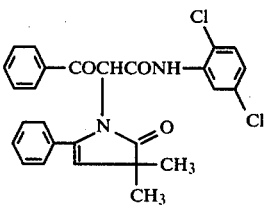 Y-106
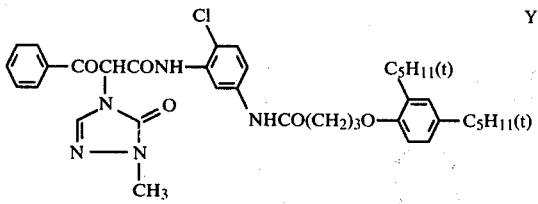 Y-107
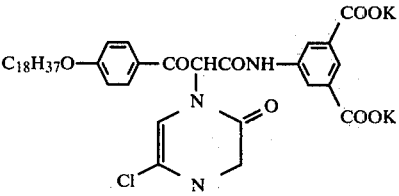 Y-108
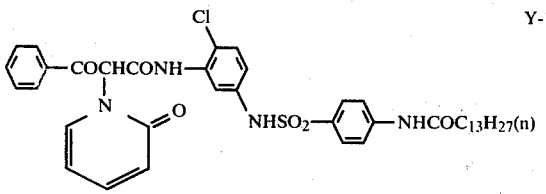 Y-109
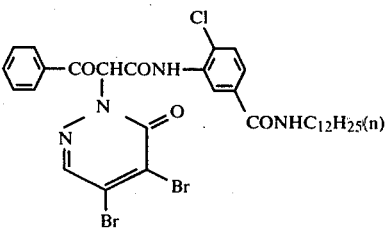 Y-110

-continued
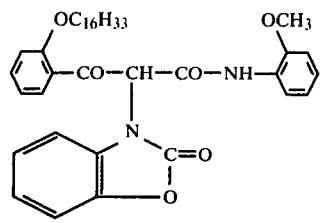 Y-111
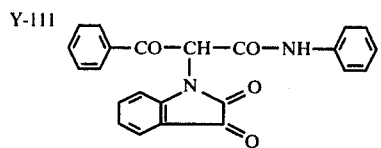 Y-112
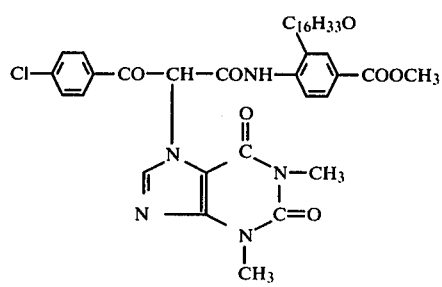 Y-113
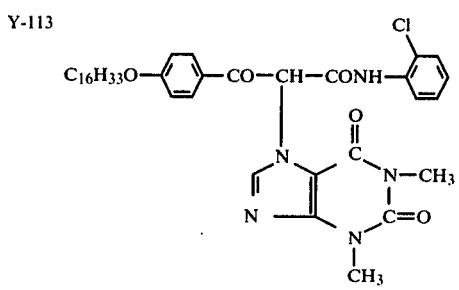 Y-114
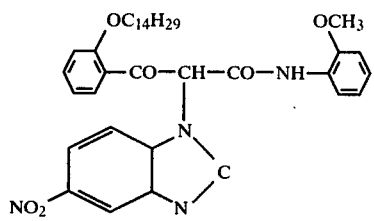 Y-115
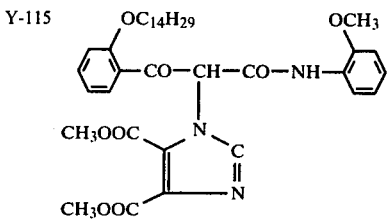 Y-116
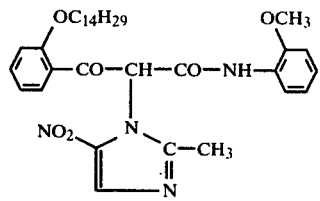 Y-117
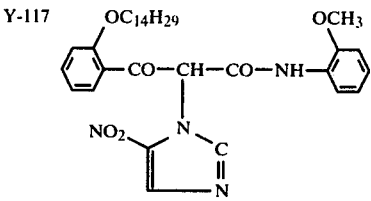 Y-118
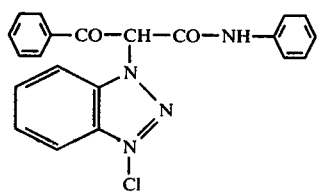 Y-119
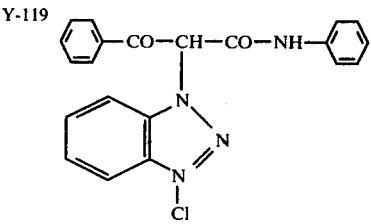 Y-120
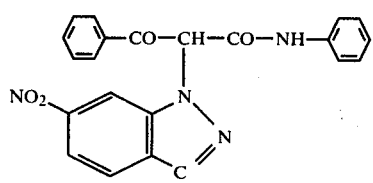 Y-121
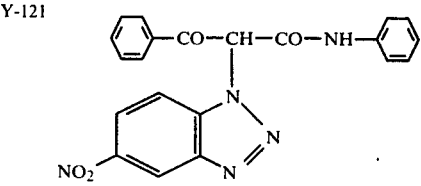 Y-122
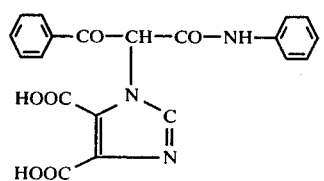 Y-123
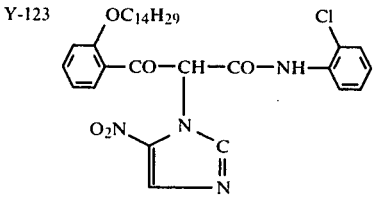 Y-124

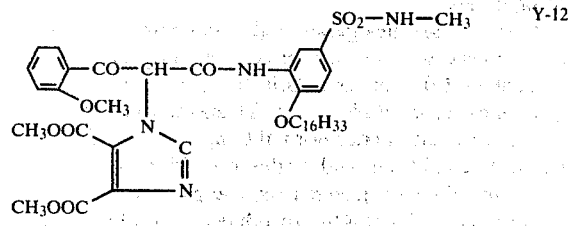
Y-125

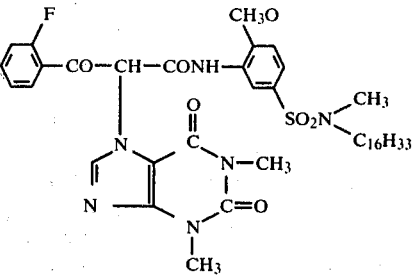
Y-126

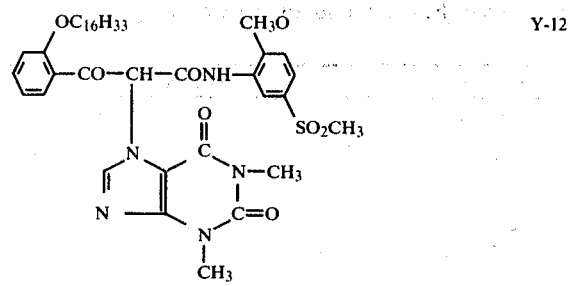
Y-127

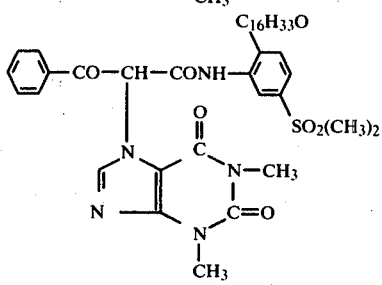
Y-128

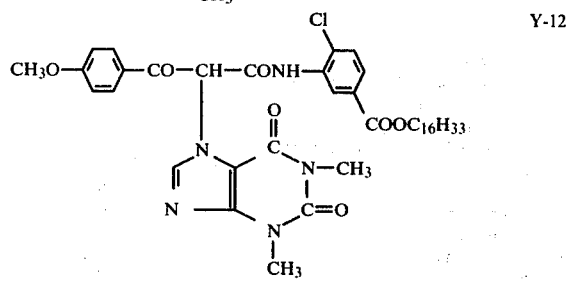
Y-129

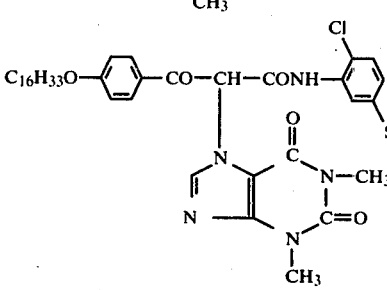
Y-130

These yellow couplers are readily prepared according to any of methods described, for example, in German Laid-open Patent Publication Nos. 2,057,941 and 2,163,812 and Japanese Laid-open Patent Application Nos. 47-26,133, 48-66,834, 50-28,834, 50-104,026, 50-158,329, 51-3,631, 50-34,232 and 51-53,825.

These couplers are incorporated in a color photographic material in any of known way such as described in, for example, U.S. Pat. Nos. 2,304,939, 2,322,027, 2,801,171 and 2,949,360, and German Pat. No. 1,143,707. In addition, there is also used a method in which couplers are dissolved in synthetic polymers such as, for example, a copolymer of butylacrylate and hydroxyethylmethacrylate with the aid of an organic auxiliary solvent.

The compounds of the general formula (I) used in the present invention may be applied by adding them to an emulsion after being dissolved in organic solvents such as methanol, ethanol, methyl cellosolve, dimethylformamide and the like, or after being solubilized with anionic surface active agents, or by adding them to an emulsion after being dissolved in oily solvents together with couplers and then converted into an aqueous dispersion with use of surface active agents.

Though the amount to be incorporated varies depending on the type of an emulsion used and the manner of addition, it is generally desirable to be in the range of 1 mg–100 mg per mole of silver halide when added to at the time of physical ripening or in the range of 2 mg–500 mg when added to during the chemical ripening or during a time of from completion of the chemical ripening before coating.

The silver halides to be contained in the silver halide emulsion layer according to the invention may be any of silver iodobromide, silver chlorobromide, silver bromide, silver chloroiodobromide and silver chloride.

These silver halides are usually dispersed in binders such as gelatin. The photographic emulsion of silver halides dispersed in a suitable binder may be chemically sensitized with chemical sensitizers, such as noble metal sensitizers, sulfur sensitizers, selenium sensitizers, and reduction sensitizers. Further, a spectral sensitizing method which has been usually employed for color photographic photosensitive materials may be applied. In addition, incorporation of stabilizers such as triazoles, azaindenes or the like compounds, which are not included within the scope of the invention, together with the fog inhibitors of the general formula (I) according to the invention is effective in suppressing a variation of sensitivity and an increase of fogging as will be experienced on preservation of color photographic photosensitive materials.

To the silver halide emulsion may be added various other additives for photography, for example, a hardening agent, a surface active agent, an antifoggant and other additives such as an UV absorber and a fluorescent whitening agent.

The silver halide photographic emulsion according to the invention is generally applied to a suitable support and dried to give a color photographic photosensitive material. The supports are those of paper, cellulose acetate, polyester, laminates of two or more base materials such as paper and polyolefins (polyethylene, polypropylene and the like).

The silver halide photographic emulsion is coated on the support and dried to obtain a photographic material.

The color photographic photosensitive materials according to the invention are basically arranged as described hereinabove. The color photographic photosensitive materials may further include combinations of green-sensitive and red-sensitive silver halide photographic emulsion layers which are spectrally sensitized to an extent of a range of other wavelengths, an intermediate layer, a protective layer, a filter layer, an antihalation layer, and a backing layer.

The color photographic photosensitive material according to the invention is developed to produce a color image after exposure. The developing treatment fundamentally includes color development, bleaching and fixing steps. The treating temperature is set in a preferred range depending on the type of the photosensitive material and the manner of treatment. Usually, the temperature is in the range of 20° C.–60° C. The photosensitive materials according to the invention are suitable for the treatment particularly at above 30° C.

The present invention will be particularly illustrated by way of the following examples.

In these examples, there are used for comparative purpose compounds of the following formulae which are similar to the antifoggants of the general formula (I) according to the present invention.

Comparative Compound

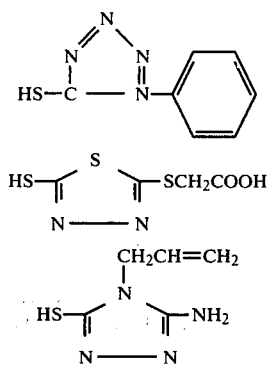

1-A

1-B

1-C

EXAMPLE 1

A 15 mole % silver chloride-containing silver chlorobromide emulsion (containing 0.25 moles of the silver halide with an average particle size of 0.6μ and 100 g of gelatin both per kg of the emulsion) was sulfur sensitized according to a usual manner, to which was added 4-hydroxy-6-methyl-1,3,3a,7-tetrazaindene, followed by dividing into several portions. Then, fog inhibitors according to the invention and comparative compounds were each added to each portion as indicated in Table 1 to prepare emulsions containing the respective fog inhibitors.

Thereafter, a 2-equivalent α-acylacetamide yellow coupler (exemplified coupler Y-21) to be used in the invention was dissolved in dibutyl phthalate and ethyl acetate, and was emulsified and dispersed in a gelatin solution by the use of sodium alkylbenenesulfonate. The resulting dispersion was added to the respective emulsions in such a manner that the coupler was 0.3 moles in amount per mole of the silver halide, to which was further added a hardening agent to prepare an application solution. These application solutions were each applied onto a photographic paper support covered with a polyethylene film so that the amounts of the metallic silver and gelatin were 0.35 g/m² and 1.3 g/m², respectively.

Then, an aqueous gelatin solution containing a hardening agent was applied, as a protecting layer, in an amount of 1.0 g/m² as gelatin thereby providing samples for experiment Nos. 1–14. These samples were each stored for 3 days under normal temperature and normal hubidity conditions and under conditions of 50° and 80%, and then subjected to a wedge exposure in the Sensitometer Model KS-7 (produced and sold by Konishiroku Photo Industry Co. Ltd.) and a color development according to the following treating procedures.

| Treating procedure | Temperature | Time |
|---|---|---|
| Color development | 33° C. | 3 min. and 30 sec. |
| Bleaching fixation | 33° C. | 1 min. and 30 sec. |
| Washing | 33° C. | 3 min. |
| Drying | 30–120° C. | |
| Color developer solution | | |
| Benzyl alcohol | | 15 ml |
| Ethylene glycol | | 15 ml. |
| Whitex BB* (50% solution) (Whitening agent*, commercial name of Sumitomo Chem. Co., Ltd.) | | 2 ml |
| Hydroxylaminesulfate | | 3 g |
| 3-Methyl-4-amino-N-ethyl-N-(β-methanesulfonamidoethyl)aniline sulfate | | 4.5 g |
| p-Toluenesulfonic acid | | 10.0 g |
| Potassium carbonate | | 30 g |
| Potassium sulfite | | 2 g |
| Potassium bromide | | 0.5 g |
| Potassium chloride | | 0.5 g |
| 1-Hydroxyethylidene-1,1-diphosphonic acid (60% aqueous solution) | | 2 ml |

Water was added for making up to 1 l. and the pH of the solution was adjusted to 10.2 by means of a sulfuric acid or potassium hydroxide solution.

| Bleaching-fixing solution | |
|---|---|
| Ethylenediaminetetraacetic acid | 40 g |
| Ammonium sulfite (40% solution) | 35 ml |
| Ammonium thiosulfate (70% solution) | 135 ml |
| Sodium (ethylenediaminetetraacetate) iron (III) complex | 70 g |
| Ammonia water (28%) | 35 ml |

Water was added for making up to 1 l. and ammonia water or glacial acetic acid was used to adjust its pH to 7.

The reflection density of each of yellow images formed on the respective samples was measured by means of the Sakura Color Densitometer Model PDA-60 (made by Konishiroku Photo Inc. Co., Ltd.) using a blue filter to determine a specific sensitivity, a maximum density and a degree of fog. The results are shown in Table 1. In the column A of the table, the specific sensitivity is expressed in terms of a relative sensitivity when the sample No. 14 which is free of any fog inhibitor is kept under normal temperature and normal humidity conditions and its sensitivity is taken as 100, while, in the column B, the specific sensitivity is expressed in terms of a relative value when the sensitivity (sensitivity in column A) of each sample kept under normal temperature and normal humidity conditions is taken as 100.

TABLE 1

| Sample No. | Added compound Amount of compound (mg/mole of silver halide) | | A. stored under normal temperature and normal humidity conditions for 3 days | | | B. stored under conditions of 50° C. and 80% for 3 days | | |
|---|---|---|---|---|---|---|---|---|
| | | | Specific sensitivity | Maximum density | Fog | Specific sensitivity | Maximum density | Fog |
| 1. | Exemplified compound 3 | 10 | 98 | 2.42 | 0.05 | 99 | 2.38 | 0.07 |
| 2. | | 50 | 92 | 2.42 | 0.03 | 100 | 2.41 | 0.05 |
| 3. | | 100 | 85 | 2.38 | 0.02 | 100 | 2.36 | 0.03 |
| 4. | Exemplified compound 11 | 10 | 100 | 2.43 | 0.06 | 100 | 2.39 | 0.07 |
| 5. | | 50 | 96 | 2.42 | 0.04 | 98 | 2.40 | 0.05 |
| 6. | | 100 | 91 | 2.40 | 0.02 | 100 | 2.39 | 0.04 |
| 7. | Exemplified compound 17 | 10 | 98 | 2.41 | 0.05 | 99 | 2.37 | 0.07 |
| 8. | | 50 | 94 | 2.41 | 0.03 | 100 | 2.38 | 0.04 |
| 9. | | 100 | 87 | 2.37 | 0.03 | 100 | 2.37 | 0.04 |
| 10. | Comparative compound 1-A | 10 | 90 | 2.38 | 0.09 | 98 | 2.36 | 0.16 |
| 11. | | 100 | 73 | 2.35 | 0.16 | 100 | 2.24 | 0.32 |
| 12. | Comparative compound 1-B | 10 | 97 | 2.41 | 0.08 | 99 | 2.38 | 0.16 |
| 13. | | 100 | 89 | 2.39 | 0.06 | 98 | 2.33 | 0.15 |
| 14. | — | | 100 | 2.43 | 0.10 | 98 | 2.35 | 0.19 |

From the above table, it will be understood that the sample Nos. 1-9 using the fog inhibitors according to the invention can suppress the fog to a much more extent than the sample No. 14 using no fog inhibitor, and are smaller in reductions of the sensitivity and density and show a more pronounced fog-inhibiting effect than the sample Nos. 10-13 using the comparative compounds.

EXAMPLE 2

The sample No. 6 (containing the fog inhibitor and the 2-equivalent α-acylacetamide yellow coupler according to the invention in amounts of 100 mg and 0.3 moles per mole of silver halide, respectively), the sample No. 13 (containing the comparative compound 1-B in an amount of 100 mg per mole of silver halide) and the sample No. 14 (free of any fog inhibitor) each used in Example 1 were exposed in an imagewise pattern, after which 2 $m^2$ of each of the samples was treated with 1 l. of a color developer without adding any making-up solution.

Then, the Sakura Color Paper Type QIII (product of Konishiroku Photo. Inc. Co., Ltd.) was subjected to a wedge exposure using a suitable color correction filter, followed by developing the same treating procedure as in Example 1 using each of the color developers which had been used to treat the sample Nos. 6, 13 and 14 and a bleaching-fixing solution of the same composition as in Example 1.

The reflection densities of a yellow image, a magenta image and a cyan image formed on the Sakura Color Paper Type QIII which had been treated with each of the color developers used to treat the sample Nos. 6, 13 and 14 were measured by means of the Sakura Color Densitometer Model PDA-60 (made by Konishiroku Photo. Inc. Co., Ltd.) using an attached blue filter, green filter and red filter, with the results of specific sensitivities and fog shown in Table 2.

| Color Developer Solution | |
|---|---|
| Benzyl alcohol | 20 ml |
| Ethylene glycol | 15 ml |
| Whitex BB* (50% solution) (commercial name of Sumitomo Chem. Co., Ltd.*) | 2 ml |
| Hydroxylamine sulfate | 4 g |
| 3-Methyl-4-amino-N-ethyl-N-(β-methanesulfonamidoethyl) aniline sulfate | 7 g |
| p-Toluenesulfonic acid | 10 g |
| Potassium carbonate | 30 g |
| Potassium sulfite | 2 g |
| 1-Hydroxyethylidene-1,1-diphosphonic acid (60% aqueous solution) | 2 ml |

Water was added for making up to 1 l. and a sulfuric acid or potassium hydroxide solution was used to adjust its pH.

TABLE 2

| Sample No. | Tested sample | Specific sensitivity* | | | Fog | | |
|---|---|---|---|---|---|---|---|
| | | Pan | Ortho | Regular | Pan | Ortho | Regular |
| 15 | Sakura Color Paper Type QIII treated with a color developer used for treating the sample No. 6 (containing the fog inhibitor of the invention) | 98 | 98 | 100 | 0.04 | 0.05 | 0.08 |
| 16 | Sakura Color paper Type QIII treated with a color developer used for treating the sample No. 13 (containing the comparative compound) | 87 | 93 | 97 | 0.03 | 0.05 | 0.08 |
| 17 | Sakura Color Paper | | | | | | |

TABLE 2-continued

| Sample No. | Tested sample | Specific sensitivity* | | | Fog | | |
|---|---|---|---|---|---|---|---|
| | | Pan | Ortho | Regular | Pan | Ortho | Regular |
| | Type QIII treated with a color developer used for treating the sample No. 14 (containing no fog inhibitor) | 100 | 100 | 100 | 0.04 | 0.05 | 0.08 |

(Note)
*Specific sensitivities in case where the sensitivities of the sample No. 17 as pan, ortho and regular were taken as 100.

From the table, it will be seen that when the treatment is conducted using the developer which has been used for treating a great deal of the sample No. 16 or the sample using, as the fog inhibitor, the mercapto compound bearing a water-soluble group, the sensitivity for the red sensitive emulsion is more reduced than in the case of the other layers, resulting in unbalanced sensitivities. In this connection, however, even though there is used the developer which has treated a great number of the sample No. 15, i.e. the sample containing the fog inhibitor according to the invention, almost no variation in sensitivity takes place with good results.

EXAMPLE 3

A 7 mole % silver iodide-containing silver iodobromide emulsion (having an average particle size of 1.2 μ and containing 0.25 moles of silver halide and 60% of gelatin both per kg of the emulsion) was prepared by a usual manner. One kilogram of the emulsion was chemically sensitized with gold and sulfur sensitizers, to which was added 0.25 g of 4-hydroxy-6-methyl-1,3,3a,7-tetrazaindene, followed by dividing into several portions. Thereafter, fog inhibitors according to the invention and comparative compounds were added to the respective portions to give several emulsions containing different types of the fog inhibitors.

Then, several types of yellow couplers substituted with nitrogen at their active centre were each dissolved in dibutyl phthalate and ethyl acetate and then emulsified and dispersed in a gelatin solution using sodium alkylbenzenesulfonate. These dispersions and the emulsions were combined to give combinations of the fog inhibitors and the couplers indicated in Table 3 thereby providing application solutions each containing 0.3 moles of the coupler per mole of silver halide. These application solutions were each applied onto an acetylcellulose support so that the amount of silver was 0.6 g/m² and that of gelatin was 1.2 g/m².

Then, a gelatin aqueous solution containing a hardener was applied as a protecting layer in an amount of gelatin of 1.0 g/m² to give sample Nos. 18–24. These samples were each subjected to a white exposure through a light wedge and then to a color development according to the following treating procedures.

| Treating step (38° C.) | Treating time |
|---|---|
| Color development | 3 min. and 15 sec. |
| Bleaching | 6 min. and 30 sec. |
| Washing with water | 3 min. and 15 sec. |
| Fixation | 6 min. and 30 sec. |
| Washing with water | 3 min. and 15 sec. |
| Stabilization | 1 min. and 30 sec. |

The compositions of the treating solutions used in the respective treating steps were as follows.

| Color developer composition: | |
|---|---|
| 4-Amino-3-methyl-N-ethyl-N-(β-hydroxyethyl)-aniline sulfate | 4.8 g |
| Anhydrous sodium sulfite | 0.14 g |
| Hydroxyamine ½ sulfate | 1.98 g |
| Sulfuric acid | 0.74 g |
| Anhydrous potassium carbonate | 28.85 g |
| Anhydrous potassium bicarbonate | 3.46 g |
| Anhydrous potassium sulfite | 5.10 g |
| Potassium bromide | 1.16 g |
| Sodium chloride | 1.14 g |
| Trisodium nitrilotriacetate (monohydrate) | 1.20 g |
| Potassium hydroxide | 1.48 g |
| Making up to 1 l. with water. | |

| Composition of bleaching solution: | |
|---|---|
| Ammonium (ethylenediaminetetraacetate) iron complex | 100.0 g |
| Diammonium ethylenediaminetetraacetate | 10.0 g |
| Ammonium bromide | 150.0 g |
| Glacial acetic acid | 10.0 ml |

Water was added for making up to 1 l. and ammonia water was used to adjust its pH to 6.0.

| Composition of fixing solution: | |
|---|---|
| Ammonium thiosulfate | 175.0 g |
| Anhydrous sodium sulfite | 8.6 g |
| Sodium metasulfite | 2.3 g |

Water was added for making up to 1 l. and acetic acid was used for adjusting its pH to 6.0.

| Composition of stabilizing solution: | |
|---|---|
| Formalin (37% aqueous solution) | 1.5 ml |
| Konidax (product of Konishiroku Photo Industry Co., Ltd.) | 7.5 ml |

Water was added for making up to 1 l.

The reflection densities of yellow images formed on the respective samples were measured by means of the Sakura Color Densitometer Model PDA-60 (made by Konishiroku Photo Industry Co., Ltd.) using an attached blue filter with the results of specific sensitivity and fog shown in Table 3.

In the table, the specific sensitivity was expressed in terms of a relative value when the sensitivity of the sample No. 24 using no fog inhibitor was taken as 100.

TABLE 3

| Sample No. | Fog inhibitor Compound | Amount (mg/mole of silver halide) | Coupler | Specific sensitivity | Fog |
|---|---|---|---|---|---|
| 18 | Exemplified compound 18 | 50 mg | Exemplified coupler Y-32 | 96 | 0.06 |
| 19 | Exemplified compound 18 | 50 mg | Exemplified coupler Y-21 | 94 | 0.05 |
| 20 | Exemplified compound 2 | 50 mg | Exemplified coupler Y-5 | 95 | 0.06 |
| 21 | Exemplified compound 2 | 50 mg | Exemplified coupler Y-21 | 95 | 0.05 |
| 22 | Exemplified compound 2 | 50 mg | Exemplified coupler Y-32 | 96 | 0.06 |
| 23 | Comparative compound 1-C | 50 mg | Exemplified coupler Y-32 | 89 | 0.13 |
| 24 | | | Exemplified coupler Y-32 | 100 | 0.10 |

As will be apparent from the results shown in the table, the samples 18–22 using combinations of the fog inhibitors and Y-couplers according to the invention are effective in suppressing the fog phenomenon more considerably than the sample 24 using no fog inhibitor in combination and are low in reduction of sensitivity, while the sample 23 using the comparative compound and the Y-coupler in combination is found not only to show little fog-suppressing effect, but also to be great in desensitivity.

EXAMPLE 4

A photographic paper support covered with an aphthase-type titanium oxide-containing polyethylene film was subjected to a corona discharge to pretreat the surface polyethylene film, on which was coated the following layers in this order form the side of the support to provide a sample No. 25.

Layer-1

Blue-sensitive silver halide emulsion layer

A 90 mole % silver halide-containing silver chlorobromide emulsion (containing 0.25 moles of silver halide with an average particle size of 0.6 $\mu$ and 100 g of gelatin per kg of the dispersion) was prepared by a usual manner.

1 kg Of the emulsion was sensitized with a sulfur sensitizer, to which were added as a blue sensitive dye sensitizer $6.3 \times 10^{-5}$ moles of anhydro-5-methoxy-5'-methyl-3,3'-di(3-sulfopropyl)selanacyanine-hydroxide sodium salt and further 0.2 g of 4-hydroxy-6-methyl-1,3,3a7-tetrazaindene and 11.6 mg of the exemplified compound. Further, there was added a dispersion, in dibutyl phthalate, of 0.25 moles of the exemplified yellow coupler Y-21 per mole of the silver halide and 0.15 moles of 2,6-di-t-octylhydroquinone (as an anti-color stain agent) per mole of the coupler. The resulting dispersion was applied to so that an amount of silver after drying was 0.4 g/m² as metallic silver, an amount of gelatin was 1.5 g/m², and the film thickness was 2.5 $\mu$.

Layer-2

Intermediate layer

An aqueous gelatin solution was applied to in an amount of gelatin of 1.0 g/m² in a dry film thickness of 1.0 $\mu$.

Layer-3

Green sensitive silver halide emulsion layer

A 20 mole % silver chloride-containing silver chlorobromide dispersion (containing 0.25 moles of silver halide with an average particle size of 0.3 $\mu$ and 125 g of gelatin per kg of the dispersion) was prepared by a usual manner.

The emulsion was sulfur sensitized, to which was added as a green sensitive dye sensitizer anhydro-5,5'-diphenyl-9-ethyl-3,3'-(di-$\gamma$-sulfopropyl)oxa-carbocyaninehydroxide. In addition, 4-hydroxy-6-methyl-1,3,3a,7-tetrazaindene to render the emulsion green-sensitive, to which was further added a magenta coupler of 1-(2,4,6-trichlorophenyl)-3-(2-chloro-5-octadecenyl-succinimido-anilino)-5-pyrazolone dispersed in a 2:1 mixed solution of butyl phthalate and tricresyl phosphate in an amount of 0.2 moles per mole of the silver halide. To the dispersion were added an anti-color stain agent of 2,5-di-t-octyl-hydroquinone dispersed in the same mixed solution as indicated above in an amount of 0.3 moles per mole of the coupler and an antioxidant of 2,2,4-trimethyl-6-lauroxy-7-octylchromane in an amount of 0.5 moles per mole of the coupler. The resulting dispersion was applied to in such an amount that, after drying, the amount of silver was 0.3 g/m² as metallic silver, the amount of gelatin was 1.4 g/m² and the film thickness was 2.4 $\mu$.

Layer-4

Intermediate layer

A gelatin aqueous solution was applied to in an amount of gelatin of 2.0 g/m² and in a dry film thickness of 2.0 $\mu$.

Layer-5

Red sensitive silver halide emulsion layer

A 20 mole % silver chloride-containing silver chlorobromide emulsion (containing 0.25 moles of silver chlorobromide with an average particle size of 0.2 $\mu$ and 125 g of gelatin per kg of the dispersion) was prepared by a usual manner.

The emulsion was sulfur sensitized, to which were added as a red sensitive dye sensitizer 3-ethyl-1'-carbamoylmethyl-4,5-benzothia-4'-carbocyanine chloride and then 4-hydroxy-6-methyl-1,3,3a,7-tetrazaindene to render it red sensitive, followed by dispersing, simultaneously in dibutyl phthalate, a cyan coupler of 2,4-dichloro-3-methyl-6-[$\alpha$-(2,4-di-t-amylphenoxy)-butylamido]-phenyl and an anti-color stain agent of 2,5-di-t-octyl-hydroquinone in an amount of 0.1 mole per mole of the coupler, the coupler being added in an amount of 0.2 moles per mole of the silver halide. The emulsion was applied to in such a manner that, after drying, the amount of silver was 0.25 g/m² as metallic silver, the amount of gelatin was 1.2 g/m² and the film thickness was 1.5 $\mu$.

Layer-6

Protective layer

A gelatin aqueous solution was applied to in an amount of gelatin of 2.0 g/m² and in a dry film thickness of 2.0 μ.

The layers 1–6 were each incorporated with, aside from the components mentioned, bis(vinylsulfonylmethyl) ether as a hardener and saponin as coating aid.

Sample Nos. 26–28

The exemplified compound 11 used in the first layer of the sample No. 25 was replaced by compounds indicated in Table 4 to provide sample Nos. 26–28.

The four types of the samples were each exposed through a light wedge to blue light, green light and red light by the use of the Sensitometer Model KS-7 (made by Konishiroku Photo Industry Co., Ltd.) and then to a color development according to the procedures as in Example 1. Thereafter, the reflective densities of dye images of the blue sensitive emulsions formed on the respective samples were each measured by means of the Sakura Color Densitometer Model PDA-60 (made by Konishiroku Photo Industry Co., Ltd.) using an attached blue filter, with the results shown in Table 4. In the table, the specific sensitivity was expressed in terms of a relative value when the sensitivity of the sample No. 28 which was free of any fog inhibitor was taken as 100.

TABLE 4

| Sample No. | Compound | Specific sensitivity | Fog |
|---|---|---|---|
| 25 | Exemplified compound 11 | 98 | 0.05 |
| 26 | Exemplified compound 3 | 96 | 0.04 |
| 27 | Exemplified compound 13 | 99 | 0.06 |
| 28 | — | 100 | 0.10 |

From the table, it will be appreciated that the sample Nos. 25–27 are scarcely lowered in sensitivity as compared with the comparative sample No. 28 and thus shown an excellent fob-inhibiting effect.

What we claim is:

1. A color photographic material comprising, on a support, a silver halide emulsion layer which contains a 2-equivalent α-acylacetamide yellow coupler carrying such a group, joined to a nitrogen atom, as being releasable upon the reaction with an oxidation product of a color developing agent and a compound of the following formula (I) or its tautomer:

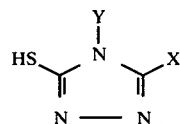

in which X represents an -NHCOR₁ radical or an -NHSO₂R₂ radical wherein $R_1$ and $R_2$ independently represent an alkyl, aryl, cycloalkyl, aralkyl or alkenyl group which may be substituted; Y represents as hydrogen atom, an alkyl, aryl, cycloalkyl, alkenyl or aralkyl group, or a —COR₃ or —SO₂R₄ radical wherein $R_3$ and $R_4$ independently represent an alkyl, aryl, alkenyl or cycloalkyl group which may be substituted, said yellow coupler containing the radical

as the coupling off group, wherein $A_1$ is a group of non-metallic atoms required to form a nitrogen-containing heterocyclic ring, which may further contain a nitrogen, oxygen or sulfur heteroatom.

2. A color photographic material according to claim 1 wherein $R_1$ and $R_2$ independently represent an alkyl or aryl group which may be substituted.

3. A color photographic material according to claim 1 wherein the 2-equivalent α-acylacetamide yellow coupler is represented by the following general formula (II)

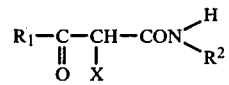

wherein $R_1$ is a linear or cyclic alkyl group carrying at its end a tertiary carbon atom directly connected to the carbonyl group selected from the group consisting of a tert-butyl group, a tert-amyl group, an 1,1-dimethylhexyl group, an 1,1-dimethyldecyl group, an 1,1-dimethyltetradecyl group, an 1,1-dimethylhexadecyl group, an 1-bicyclo(3,2,1)octyl group, a 5-norbornene-2-yl group, a 5-pinanyl group, an 1-p-menthene-8-yl group, and a bicyclo(3,2,1)oct-5-yl group, or an aryl group selected from the group consisting of a phenyl group, and a naphthyl group, $R_2$ is an aryl group selected from the group consisting of a phenyl group, a naphthyl group or a heterocyclic group selected from the group consisting of a thienyl group, a benzothienyl group, a furyl group, a pyranyl group, a pyrrolyl group, an imidazolyl group, a pyrazolyl group, a pyridyl group, a pyrimidyl group, a pyridazyl group, an indolyl group, an indazolyl group, a quinolyl group, an oxazolyl group, a pyrrolidyl group, a benzoimidazolyl group, a naphthoimidazolyl group, a benzoxazolyl, a naphthoxazolyl group, a thiazolyl group, a benzothiazolyl group, a naphtothiazolyl group, a selenazolyl group, and a benzoselenazolyl group and X is

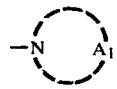

in which $A_1$ is a group of nonmetallic atoms required to form a 4- to 6-membered, nitrogen-containing heterocyclic ring, which may further contain a nitrogen, oxygen or sulfur atom as a hetero atom, and which ring may have a substituent.

* * * * *